United States Patent [19]

Alais

[11] 4,119,938

[45] Oct. 10, 1978

[54] METHODS AND DEVICES FOR ULTRASONIC IMAGING

[75] Inventor: Pierre Alais, Dampierre, France

[73] Assignee: Agence Nationale de Valorisation de la Rechere (ANVAR), France

[21] Appl. No.: 629,599

[22] Filed: Nov. 6, 1975

[30] Foreign Application Priority Data

Nov. 28, 1974 [FR] France .............................. 74 39014

[51] Int. Cl.² .............................................. G01N 29/04
[52] U.S. Cl. ..................................... 340/1 R; 340/5 H; 340/5 MP; 343/17; 358/112; 73/620; 73/629
[58] Field of Search ........................... 178/6, DIG. 18; 348/5 H, 5 MP, 6 TV, 1 R; 343/17, 113; 73/67.8 R, 67.7 S, 67.9; 358/112

[56] References Cited

U.S. PATENT DOCUMENTS 3,911,730  10/1975  Niklas .................................. 73/67.7

Primary Examiner—Benedict V. Safourek
Assistant Examiner—Edward L. Coles

Attorney, Agent, or Firm—Ostrolenk, Faber, Gerb & Soffen

[57] ABSTRACT

N elementary transducers are distributed regularly along a line of scanning. An ultrasonic frequency generator generates a high frequency signal which is applied to a first set of switches with a phase angle $\phi$ and to a second set of switches with a phase angle $\phi + \pi$. First and second registers are provided for temporarily energizing selected ones of said first and second set of switches such that the high frequency signal is applied to a set of $n$ transducers with a phase angle of either $\phi$ or $\phi + \pi$. Third and fourth registers stored a phase distribution signal which is serially clocked into and through the first and second registers such that the high frequency signal is applied to $n$ transducers with a phase distribution determined by said stored distribution signal at each of a plurality of successive times, each time to a set of $n$ transducers which is shifted by one transducer of the array of transducers such that scanning occurs throughout the array.

23 Claims, 6 Drawing Figures

METHODS AND DEVICES FOR ULTRASONIC IMAGING

BACKGROUND AND SUMMARY OF THE INVENTION

The present invention relates to ultrasonic imaging with electronic scanning, enabling the exploration of a part or an organ to be analysed, notably in a plan (C scan mode echography) or in depth (B mode echography).

Such an imaging device is capable of numerous applications, particularly in the field of medicine, in which field imaging by ultrasonic offers, over imaging by ionizing radiation (including X-rays), the great advantage of not subjecting the patient to harmful radiation.

Before defining the invention, it would seem desirable to recall some theoretical considerations which relate to the ultrasonic transmitters, although they apply just as well to receivers.

It is possible to design an ultrasonic transducer device whose energy is focused along a line, using a linear array of elementary transducers each of which receives the same signal at ultrasonic frequency, via delay means which delay the signal by appropriate amounts before it is applied to the elementary transducers. The delay means may for instance be delay lines. If the number of signal alternations is high, the need for having one delay line for each elementary transducer may be overcome if it is remembered that the delay may be equal to the $2\pi$-modulo phase for each transducer and if the phase is quantified at some levels within an interval of $2\pi$. A solution is then reached which is of the type used at present in sonar and radar installations and which is quite complex.

There is also known a device for ultrasonic monitoring of tubes (French Pat. No. 1,593,804) which comprises transducers which are successively energized, one at a time, each with a suitable time lag. This arrangement requires the creation of a large number of phase shifts, all different, which leads to an extremely complex system.

A system of submarine ultrasonic monitoring (French Pat. No. 1,569,897) is also known, which is of the "sonar" type comprising a series of elementary transducers positioned symmetrically with respect to a central transducer. On each pair of elementary transducers around the central transducer an electric signal is applied with a particular phase shift or delay. Although this device enables circular scanning to be effected, it does not, on the other hand, provide any focalization.

It is an object of the invention to provide an improved ultrasonic sounding device with electronical translation, which at the same time permits focusing and scanning in a predetermined direction while simple in construction and operation.

There is provided an ultrasonic sounding device comprising an array of N elementary transducers distributed regularly along a line of translation, means for storing the distribution over $n$ successive elementary transducers ($n$ being an integer smaller than N) of the phases corresponding to focusing at a predetermined distance from said line, ultrasonic transmit/receive means and switch means for connecting the individual transducers of any group of $n$ transducers to said transmit/receive means directly and via phase shift means according to the distribution. The phase shift means comprises inverter means causing a phase shift of $\pi$ and the storing means store the distribution of the transducers connected directly and those connected through the inverter means. The group of the $n$ elemental transducers which are energized is moved at intervals of time along said line. The translation line is generally straight; however, another curve such as a circle may be used.

Such a device is much simpler than those previously known and does not require a phase lag device, but only inverter means to produce binary phase quantization.

Not only a fundamental focusing at distance $Y_n$ is then produced, but also harmonic focusing at the distance $Y_n/3$, $Y_n/5$, . . . However, it is sufficient to provide selection with a range gate corresponding to the transit time from the transmitting transducers to the fundamental focusing point and back to the receiver transducer (which may be the same as the transmitting transducers).

The invention will be better understood on reading the description which follows of devices which constitute specific embodiments, given by way of non-limitative examples.

SHORT DESCRIPTION OF THE DRAWINGS

DETAILED DESCRIPTION OF PREFERRED EMBODIMENTS

To facilitate the understanding of the operation of the device constituting one embodiment of the invention which will be described below, the conditions to be fulfilled will first be recalled, with reference to FIG. 1.

Figure 1:
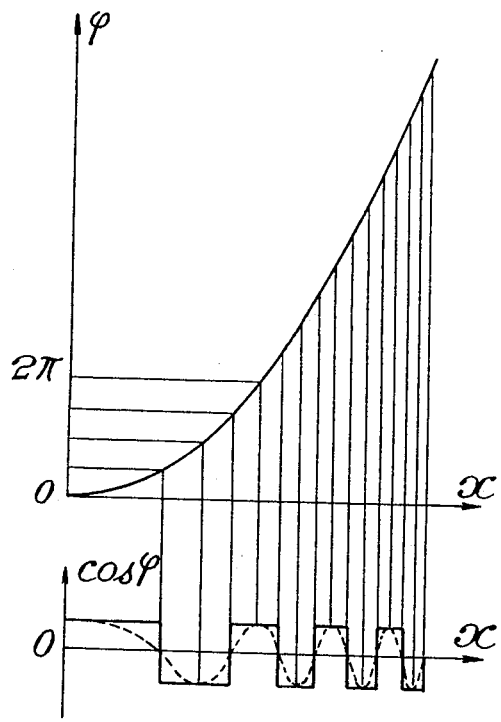
FIG. 1 is a diagram showing the variation of the phase shift $\phi$ to be produced on transducers distributed along a direction OX to cause focusing, as well as the corresponding variation of $\cos \phi$ (dashed curve) and the simulation of such variation by binary phase quantization at a single amplitude level.

FIG. 1 shows the variation of phase $\phi$ to be produced on the transducers distributed along a direction OX (as well in fact as along the symmetrical direction with respect to O) to focus an ultrasonic beam at a point M in front of O and at the distance $Y_M$ from the straight line on which the $n$ elementary transducers are distributed. If the radiation has a wave length $\lambda$ in the propagation medium concerned, each transducer of order $i$ must receive a signal whose phase lead with respect to the transducer placed at O is:

$$\phi_i = \pi x_i^2 / \lambda y$$

$x_i$ being the abscissa of the transducer with respect to O.

In other words, the complex amplitude $A_i^*$ of the signal applied to the elementary transducers of order $i$ must be:

$$A_i^* = A_o \exp(j\phi_i)$$

of which the real part $A_o \cos \phi_i$ is given by the curve in dashed line in FIG. 1.

As indicated above, it would be possible to ensure focusing at the distance $Y_m$ by effecting the phase distribution with binary quantization shown schematically in full line in FIG. 1. However, this simulation makes it necessary to provide elementary transducers whose successive lengths correspond to successive half waves and does not permit electronic scanning along the direction OX.

According to the invention, N identical transducers are distributed regularly along the direction OX; among the N transducers, $n$ adjacent transducers (64 in the embodiment given by way of example in FIG. 2) are simultaneously actuated. The number $n$ is less than N to permit scanning.

Figure 2:
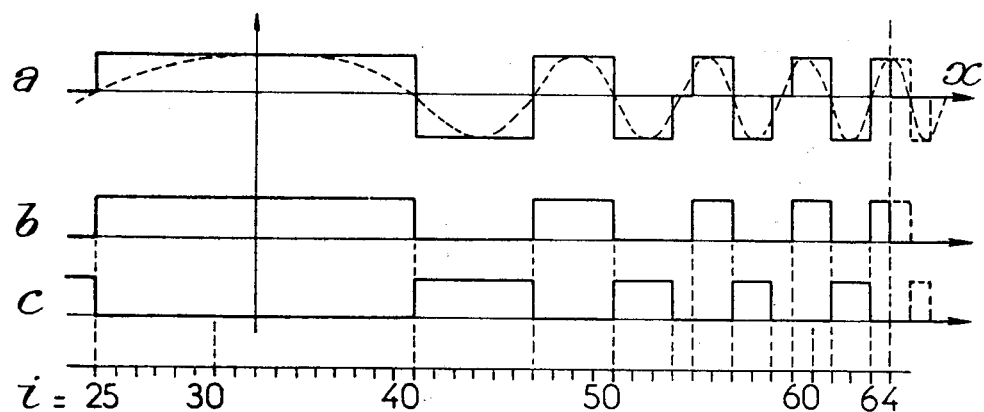
FIG. 2 shows the simulation of the phase distribution over sixty-four elementary signal transducers with binary phase quantization (line $a$) for focusing and how the distribution is achieved using two registers with sixty four binary positions (lines $b$ and $c$)

Referring to line $a$ on FIG. 2, there is shown the phase distribution to be achieved on the transducers numbered 24 to 64 distributed along a straight line to focus the ultrasonic transmission of the transducers at a point M placed in the midplane of the line, in front of the junction between the elementary transducers numbered 32 and 33. It may be seen that:

Some of the transducers must receive the signal at ultrasonic frequency with a reference phase (for example transducers 25 to 40, 47 to 50, . . .);

Some other transducers must receive the ultrasonic signal with a phase shift equal to $\pi$ with respect to the reference (for example, transducers 41 to 46, 51 to 52, . . .);

Last, the remaining transducers must receive no signal (elementary transducers numbered 54, 59 and 65).

To simplify the construction, it would be possible (at the cost of less accurate simulation), to provide that each of the elementary transducers should receive a signal, in phase or in phase opposition with the reference.

The phase distribution indicated in FIG. 2 is not the only one which ensures focusing at point M; if the use of circuits providing a $\pi/2$ phase lag is accepted, the transducers which must not receive any signal in the distribution illustrated on line $a$ of FIG. 2 can receive such a signal with a $\pi/2$ phase shift.

Figure 3:
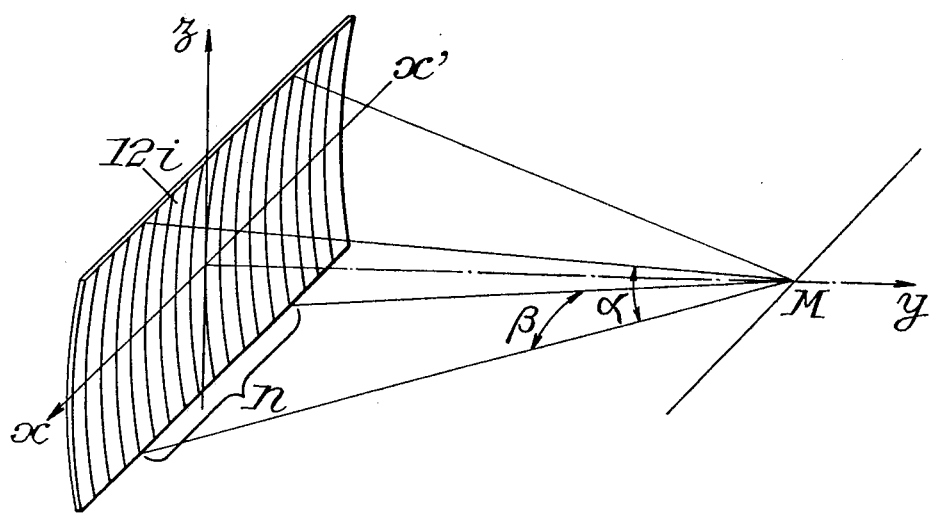
FIG. 3 shows diagrammatically how an array of elementary transducers may be formed for carrying out the invention.
Figure 4:
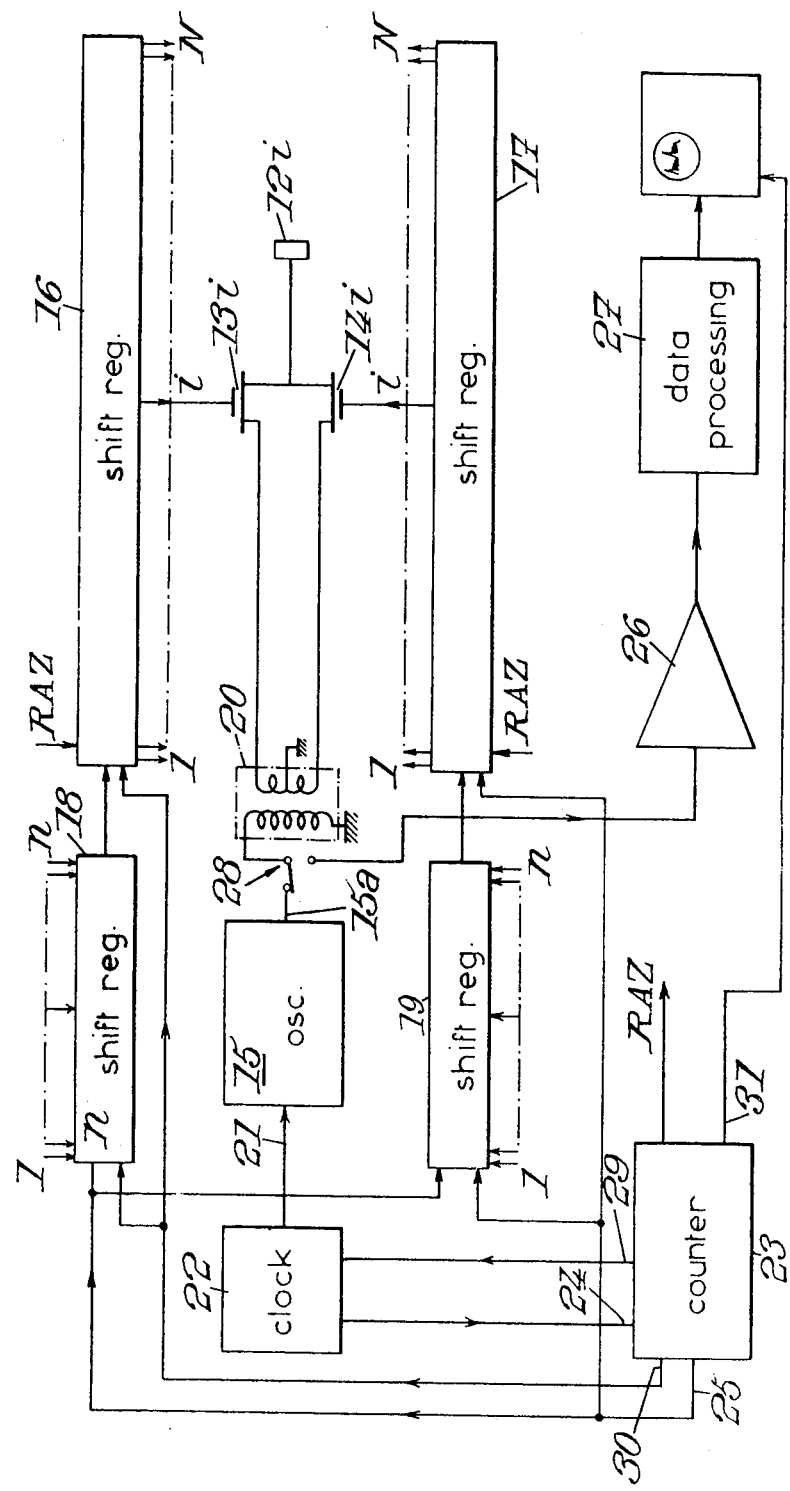
FIG. 4 is a schematic diagram of a circuit which can be associated with the transducers of FIG. 3 to produce the distribution illustrated in FIG. 2.

The distribution of FIG. 2 can be produced by means of a transducer system of the type shown diagrammatically in FIG. 3 associated with a circuit of the type shown on FIG. 4.

The transducer of FIG. 3 is designed to produce three-dimensional or space focusing at a point M and to effect electronic translocation or scanning along the direction X'X. To this end, it comprises elementary transducers shown diagrammatically by strips such as 12$i$, in the form of part-circular segments, arranged over a cylindrical surface whose axis constitutes the locus of the points M during scanning. The angular aperture $\alpha$ of the cylindrical sector is selected to ensure sufficient concentration of energy at the point M and to achieve satisfactory resolution in the direction of the axis z. The N elementary transducers may be constituted by metal strips deposited by photogravure on the concave surface of a piezo-electric ceramic support in the form of a cylindrical segment whose convex surface is wholly coated with metal. When the pitch $p$ of the strips exceeds about 1 mm, it is also possible to separate the strips by grooves cut out on a metal coated concave surface, which have the advantage of producing mechanical uncoupling.

Referring to FIG. 4, there is shown an electrical circuit for simultaneously applying suitable signals to $n$ elementary transducers of the system of FIG. 3 and for displacing this group step by step along the transducer system in direction X'X. It will be assumed for example that the distribution to be produced is that of FIG. 2, with $n = 64$ and $N = 160$.

In the circuit of FIG. 4, each transducer (such as transducer 12$i$, the only one shown) is associated with selector means constituted by two switches 13$i$ and 14$i$, one for applying to the transducer the signal at ultrasonic frequency coming from the single generator 15 with one reference phase, the other, the same signal phase-shifted by 180° with respect to the first. The switches are field effect transistors whose control electrode is connected to the binary position of order $i$ of a respective shift register (16 for the transistors 13, 17 for the transistors 14) with N binary positions. Depending whether the position $i$ of the register 16 or 17 contains a binary 1 or 0, the transistor 13$i$ or 14$i$ is unblocked or blocked.

The phase distribution to be effected over $n$ successive elementary transducers is set in two $n$-bits shift registers 18 and 19 with parallel loading; the series output of each register 18 or 19 is connected with the series input of the corresponding register 16 or 17. Loading means, for example ROM or PROM store, are associated with the registers 18 and 19. A control keyboard can also be used, the loading then being simplified since the distribution is an even function, so that each key of the keyboard can control two positions of the register 18 or 19. The registers 18 or 19 can thus be loaded in accordance with the distribution illustrated in lines $b$ and $c$ of FIG. 2.

The output of generator 15, constituted by a triggered oscillator, is connected to the transistors 13 and 14 constituting selector means through a unit supplying, from the input signal, two signal phase shifted by 180° from each other. The unit may be constituted by a transformer 20 with grounded mid-point and whose opposite output poles are connected, the one to the transistors 13, the other to the transistors 14. The triggered oscillator 15 comprises a control input 21 connected to a clock 22 which fixes the rate of emission of the ultrasonic wave trains and of the electronic translations or scanning which occur between each wave train transmission. A pulse counter or scaler 23 receives, at its input 24, the clock output pulses; its outputs 25, controls the shifts of the registers 16 and 17; its output 29 controls the operation of the clock; the counter also resets the registers 16 and 17 at the end of a complete translation sequence.

Last, the circuit of FIG. 4, intended for cooperation with a transmit/receive transducer system, comprises a receiver channel including an amplifier 26 and a processing and display circuit 27 which can be conventional. The amplifier 26 receives the signals returning to elementary transducers, through transformer 20. It has to be protected against the transmitted signals: in the embodiment illustrated, protection is provided by switch 28 controlled electronically and which it is not necessary to describe since it can be of a type quite conventional in ultrasonics.

When a transducer system of the type illustrated in FIG. 3 is used, the circuit is typically adapted so that the aperture β corresponding to the n elementary transducers operated simultaneously corresponds more or less to double the geometric aperture α. Moreover, the duration of each wave train emitted by the generator 15 will advantageously be selected so that the number of oscillations in each train is substantially equal to the number of half-waves reproduced by the n transducers supplied. For this purpose, it will be possible to associate with the generator 15 an input gate triggered by the trailing edge of each clock pulse and whose gating time period is adjustable.

The operation of a device of the type illustrated in FIGS. 3 and 4 will now be described in simplified manner; reference will be made for explanatory purpose to a transducer system constituted by a part-cylindrical segment of zirconate of about 1 mm thickness, on which strips constituting the elementary transducers are arranged with a pitch $p$ of 1.25 mm and which are separated by grooves 0.25 mm in width. The circuit of FIG. 4 then comprises, for example, a 2 MHz generator, corresponding to a wave length of 0.75 mm in water. It will also be assumed here, when reference is made to numerical data, that $n = 64$, $N = 160$ and $Y_M = 200$ mm.

Figure 5:
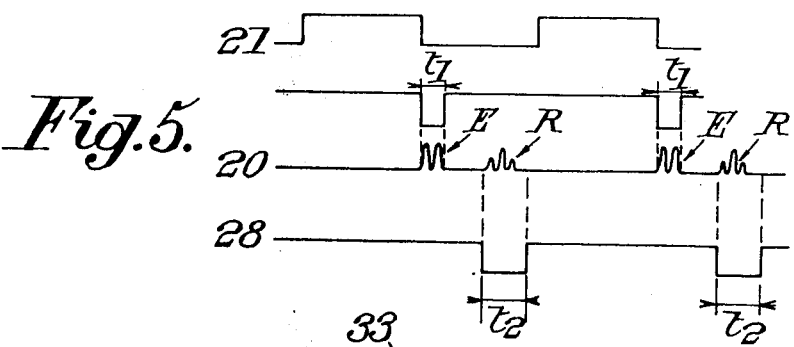
FIG. 5 is a diagram showing the shape of the signals which appear at various points on the circuit of FIG. 4 during operation.

The whole working sequence is controlled and timed by the clock 22 and the counter 23. FIG. 5 shows, for easier understanding, the shape of the signals which appear at various point of FIG. 4 whose reference numbers correspond to those of the lines of FIG. 5.

When the system is energized by an operator (using a start switch, not shown), the clock 22 sends successive pulses from its output connected to the input 24 of the counter 23. In response to the trailing edge of the first clock pulse, the count in counter 23 is increased from zero to 1 and in response the counter 23 emits at its output 25 a pulse for loading control registers 18 and 19 in parallel.

In response to each of the following $n/2$ clock pulses, the counter 23 emits at its output 30 a shift pulse which causes the transfer in series of the contents of the control registers 18 and 19 into the registers 16 and 17, respectively. At the end of that part of the operating sequence, when the counter 23 counts up to the number $n/2$, it emits at its output 29 a signal which enables a gate located between the clock output and the input gate of the triggered generator 15 (or embodied in the input gate of the generator).

On receipt of each of the following N impulses from the clock 22 (FIG. 5), the counter 23 counts up, shifts the contents of the registers 16 and 17, and enables the input gate of the generator 15 for a period $t_1$ (FIG. 5, second line). The latter then emits, in response to each clock pulse, a pulse train E on its output 28. This pulse train is communicated to those transducers 12 which are associated with a transistor 13 or 14, then conducting (with phase reversal for some of the transistors). Transmission by the transducer system starts although only half the contents of the control registers 18 and 19 have been transferred into the registers 16 and 17. Progressively as the transfer of the contents of the registers continues, greater energy is obviously focused at the point M and at the same time the latter is moved parallel to X'X.

The counter 23 is arranged to overflow when it has received N clock pulses after the start of the emission, and then emits at an RAZ or reset output a pulse for clearing the registers 16 and 17.

The switch 28 is actuated by means (not shown) so as to route, during the time interval $t_2$ representing the depth selection range gate, the echoes received by the elementary transducers 12 which were previously transmitting. Since the reflected signals are processed through transducers 12 and switches 13 and 14, they will be subjected to a phase shift according to the stored phase distribution. In numerous cases, it is possible to dispense with switch 28 and simply to protect the amplifier 26 with an input resister. The transit or range gate time window is then generated by means incorporated in the data processing system 27.

The counter 23 can include a synchronizing output 31 supplying a signal representing the contents of the counter, so as to enable a display for example. The zero reset signal may be used to actuate a mechanical movement of the transducer system by one step in the direction z.

Figure 6:
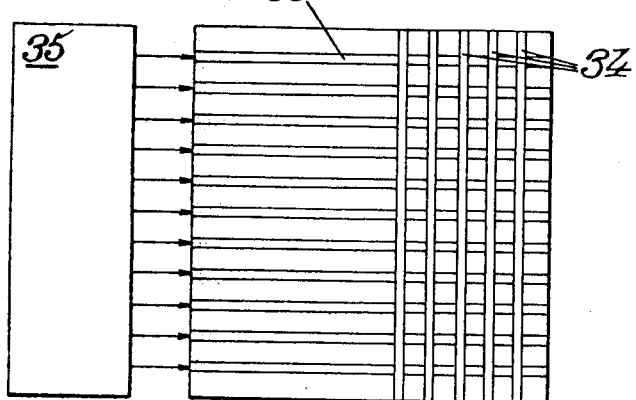
FIG. 6 shows a modification of the transducer of FIG. 3.

The circuit illustrated in FIG. 4 may also be associated with a transducer system of the type shown diagrammatically in FIG. 6. This system includes a flat plate, of piezo-electric ceramic for example, bearing one one face N horizontal metal strips constituting elementary transmitting transducers 33 and, on the opposite face, M parallel vertical strips 34 separated by insulating zones and constituting elementary receiver transducers. For improved clarity, only part of the strips are shown all in solid line, even though the strips 34 are on the front surface and the strips 33 on the rear surface.

On transmission, all of the strips 34 are grounded and the generator forming part of the circuit 35 similar to that illustrated in FIG. 4 transmits pulse trains to $n$ of the elementary transducers 33. There occurs focusing along a horizontal line (and no longer at a single point M) and vertical scanning in a plane distance $Y_M$. Two types of reception techniques can be used.

A first solution consists, after each emission of an ultrasonic wave train (which emission is repeated N times), of selecting a corresponding point M by grounding all the transducers 33 and by connecting one only of the M elementary transducers 34 to a receiver circuit 36 having a constitution similar to that shown at 26 and 27 in FIG. 4.

Another solution consists of effecting a holographic detection, which then requires M channels operating in parallel in the receiver circuit 36.

The use of an assembly comprising a transducer system of the type illustrated in FIG. 6 and a circuit of the type shown in FIG. 4 offers great flexibility of use, and renders possible to obtain great field depth and rapid modification of the focusing distance.

The field depth on transmission depends essentially on the number $n$ of transducers used in the simulation, the focusing and the resolution being all the better as the number $n$ is greater. It is possible to provide for the registers 18, 19 a capacity giving excellent resolution and, each time that there is need for great depth of field (example in B mode display) to work with a number of simultaneously actuated transducers which is much smaller, for example 32 instead of 64: to achieve this result it is sufficient to provide several ROM memories which are optionally selected for loading the control registers 18 and 19 and switching means enabling the introduction into the registers of the contents of one or other of these memories. By only using a small number of transducers, there is no actual focusing obtained, but rather a very long focal or caustic surface which may be desirable in medicine; in heart echography for example, it is necessary to have a considerable field depth to record the variable depth echoes during scanning. This result is thus obtained in a very simple manner.

However, it is also possible to preserve a high resolution by using two successive scannings (or more) in the direction x with two different phase shift distributions so as to correspond to focusing at different distances $Y_M$. For this, it suffices at the end of each scanning for the counter 23 to emit a pulse corresponding to the loading in the registers 18 and 19 of the contents of memories different from those which have just been used.

To increase the rate of picture production, it may then be advantageous to use interlacing scanning, as in current TV. For this purpose it is sufficient for the counter to be coupled to the registers so as to cause a two-bit shift between two successive sweeps and arranged so that the even lines of the frame are traversed for one picture, the odd lines for the following picture and so on. This solution also enables, by eliminating interlacing and by keeping only the even lines (or the odd lines), to return twice as fast to a point of interest whose depth is known, and consequently, to display movements.

The width of the range gate of the receiver system must obviously, in this case, be arranged to allow the passage of those echoes which correspond to the focusing zone.

It may be pointed out for example that with an interlacing device of this type it is possible to display in B mode the whole of the cardiac muscle over a depth ranging from 1 to 2 cm from the probe up to about 15 cm from the probe without difficulty.

I claim:

1. A method for ultrasonic imaging with electronic scanning using an array of N identical elementary transducers distributed at equal intervals along a scanning direction, an improved scanning process comprising the steps of:

generating a single electrical signal of frequency $f$;

storing an electrical phase distribution signal representative of the phase at which said signal of frequency $f$ is to be applied to n adjacent transducers of said array, n being an integer greater than 1 and less than N, said signal of frequency $f$ to be applied to each of said n transducers either in phase or out of phase with the remaining said n signals by $\pi$, said electrical phase distribution signal being chosen such that said n adjacent transducers focus energy at a point which is located a predetermined distance from said n transducers;

simultaneously and temporarily applying said single signal of frequency $f$ to selected ones of said set of n transducers with a phase shift dictated by said phase distribution signal; and apply said signal of frequency $f$ to n transducers at each of the plurality of successive times, each time to a set of n transducers which is shifted by at least one said transducer of said array of transducers, such that scanning occurs throughout said array.

2. A device for focusing and processing an ultrasonic image received by an array of N identical elementary ultrasonic transducers distributed at equal intervals along a scanning direction, comprising:

means for storing an electrical phase distribution signal representative of the phase shift distribution to be applied to the reflected signals received by n adjacent transducers of said array, n being an integer greater than 1 and less than N, said electrical phase distribution signal being chosen such that said n adjacent transducers focus ultrasonic energy which has a frequency $f$ and which is reflected off the object being scanned at a point which is a predetermined distance from said n adjacent transducers;

switch means coupled to each of said transducers for subjecting the reflected signals received by each of said n adjacent transducers to a phase shift of either $\phi°$ or $\phi + \pi°$ according to said electrical phase shift distribution signal, said switch means also for summing at least some of said phase shift reflected signals to form a single signal representative of a characteristic of said object being scanned;

a single receiver means responsive to said single signal;

sequencing means for causing said switch means to phase shift and combine said reflected signals received by said n adjacent transducers of said array at each of a plurality of successive times, each time from a set of n transducers which is shifted by at least one said transducer of said array of transducers such that scanning occurs through said array.

3. The device of claim 2, wherein said switch means comprises:

means for combining a plurality of electronic signals applied thereto;

a first set of N electronic switches, each of said first set of electronic switches being associated with a different one of said elementary transducers and being adapted to apply the reflected signal received by its associated transducer to said means for combining a plurality of signals with a phase angle $\phi$;

a second set of N electronic switches, each of said second set of electronic switches being associated with a different one of said N elementary transducers and being adapted to selectively apply the reflected signal received by its associated transducer to said means for combining electrical signals with the phase angle $\phi + \pi$.

4. A device for ultrasonic imaging selectively operable in both a transmitting and receiving mode, said device comprising:

(1) an array of N identical elementary transducers distributed at equal intervals along a scanning direction;

(2) a single signal generator for generating a single electrical signal of frequency $f$;

(3) a single signal receiver for processing an electronic signal at ultrasonic frequency;

(4) first switch means for selectively causing said device to operate in either said transmitting or said receiving mode;

(5) second switch means for simultaneously coupling selected ones of n adjacent transducers of said array to said first switch means, n being an integer greater than 1 and less than N;

(6) means for storing an electrical phase distribution signal representative of the phase at which said signal frequency $f$ is to be applied to each of said n adjacent transducers in said array, said electrical phase distribution signal being chosen such that said n adjacent transducers focus ultrasonic energy having a frequency $f$ at a point located at a predetermined distance from said n adjacent transducers;

(7) said second switch means also for:
  (a) causing said signal of frequency $f$ to be applied to selected ones of said $n$ adjacent transducers with a phase shift of either $\phi°$ or $\phi+\pi°$ in accordance with said electrical phase shift distribution signal when said devices operating in said transmitting mode; and
  (b) for subjecting the reflected signals received by each of said $n$ adjacent transducers to a phase shift of either $\phi°$ or $\phi+\pi°$ according to said electrical phase shift distribution signal and summing at least some of said phase shifted reflected signals to form a single signal representative of a characteristic of said object being scanned when said device is operating in said receiving mode; and
(8) sequencing means for;
  (a) causing said switch means to apply said signal of frequency $f$ to $n$ adjacent transducers of said array at each of a plurality of successive times, each time to a set of $n$ transducers which are shifted by at least one said transducer of said array of transducers, when said device is operating in said transmitting mode; and
  (b) for causing said switch means to phase shift and combine said reflected signals received by said $n$ adjacent transducers of said array at each of a plurality of successive times, each time to a set of $n$ transducers which are shifted by at least one said transducer of said array of transducers, when said device is operating in said receiving mode, such that scanning occurs throughout the said array in both said transmitting and receiving mode.

5. The device of claim 4, wherein said second switch means comprises:
  a first set of N electronic switches, each of said first set of electronic switches for selectively coupling a different one of said N elementary transducers to said first switch means with a phase angle $\phi$; and
  a second set of N electronic switches, each of said second set of electronic switches to selectively couple a different one of said N elementary transducers to said first switch means with a phase angle $\phi+\pi$.

6. A method for focusing and processing an ultrasonic image received by an array of N identical elementary ultrasonic transducers distributed at equal intervals along a scanning direction, said method comprising the steps of:
  storing an electrical phase distribution signal representative of the phase shift distribution to be applied to the reflected signals received by $n$ adjacent transducers of said array, $n$ being an integer greater than 1 and less than N, said electrical phase distribution signal being chosen such that said $n$ adjacent transducers focus ultrasonic energy which has a frequency $f$ and which is reflected off of the object being scanned at a point which is a predetermined distance from $n$ adjacent transducers;
  subjecting said reflected signals received by each of said $n$ adjacent transducers to a phase shift of either $\phi°$ or $\phi+\pi°$ according to said electrical phase shift distribution signal;
  combining at least some of said phase shifted reflected signals to form a single signal representative of a characteristic of said object being scanned; and
  applying said single signal to a single receiver at each of a plurality of successive times, each time said single signal being derived from a plurality of phase shifted signals originating from a set of said $n$ transducers which are shifted by at least one said transducer of said array of transducers, such that scanning occurs throughout the array.

7. A device for ultrasonic imaging operable in both a transmitting and receiving mode, said device comprising:
  (1) an array of N identical elementary transducers distributed at equal intervals along a scanning direction and operable at ultrasonic frequency $f$;
  (2) a single signal generator for generating a single electrical signal;
  (3) a single signal receiver for processing an electronic signal at ultrasonic frequency $f$;
  (4) switch means for simultaneously coupling selected ones of $n$ adjacent transducers of said array to said generator and receiver, in sequence, $n$ being an integer greater than 1 and less than N;
  (5) means for storing an electrical phase distribution signal representative of the phase at which said signal is to be applied to each of said $n$ adjacent transducers in said array, said electrical phase distribution signal being chosen such that said $n$ adjacent transducers focus ultrasonic energy having a frequency F at a point located at a predetermined distance from said $n$ adjacent transducers;
  (6) said switch means also for:
    (a) causing said single electrical signal to be applied to selected ones of said $n$ adjacent transducers with a phase shift of either $\phi$ or $\phi+\pi$ in accordance with said electrical phase shift distribution signal when said device operates in said transmitting mode; and
    (b) subjecting the reflected signals received by each of said $n$ adjacent transducers to a phase shift of either $\phi$ or $\phi+\pi$ according to said electrical phase shift distribution signal and summing at least some of said phase shifted reflected signals to form a single signal representative of a characteristic of said object being scanned when said device is operated in said receiving mode; and
  sequencing means for:
    (a) causing said switch means to apply said signal $f$ to $n$ adjacent transducers of said array at each of a plurality of successive times, each time to a set of $n$ transducers which are shifted by at least one said transducer of said array of transducers, when said device is operating in said transmitting mode; and
    (b) causing said switch means to phase shift and combine said reflected signals received by said $n$ adjacent transducers of said array at each of a plurality of successive times, each time to a set of $n$ transducers which are shifted by at least one said transducer of said array of transducers, when said device is operating in said receiving mode, such that scanning occurs throughout the said array in both said transmitting and receiving mode.

8. The device of claim 7, wherein said switch means comprises:
  a first set of N electronic switches, each of said first set of electronic switches for selectively coupling a different one of said N elementary transducers aaid generator or receiver with a phase angle $\phi$; and a second set of N electronic switches, each of said second set of electronic switches to selectively couple a different one of said N elementary transducers to said generator or receiver with a phase angle $\phi + \pi$.

9. The device of claim 7, wherein said switch means further comprises transformer means having a primary winding connected to said generator and said receiver and a secondary winding having opposed end terminals and a grounded central tap, one of said end terminals being connected to the first set of electronic switches and the other end terminals being connected to the second set of electronic switches.

10. A device for ultrasonic imaging comprising:

an array of N identical elementary transducers distributed at equal intervals along a scanning direction;

a single signal generator for generating a single electrical signal of frequency $f$;

switch means for simultaneously applying said signal of frequency $f$ to selected ones of $n$ adjacent transducers of said array, $n$ being an integer greater than 1 and less than N;

means for storing an electrical phase distribution signal representative of the phase at which said signal of frequency $f$ is to be applied to each of said $n$ adjacent transducers in said array, said electrical phase distribution signal being chosen such that said $n$ adjacent transducers focus ultrasonic energy having a frequency $f$ at a point located at a predetermined distance from said $n$ adjacent transducers;

said switch means also for causing said signal of frequency $f$ to be applied to selected ones of said $n$ adjacent transducers with a phase shift of either $\phi°$ or $\phi + \pi°$ in accordance with said electrical phase shift distribution signal; and sequencing means for causing said switch means to apply said signal of frequency $f$ to $n$ adjacent transducers of said array at each of a plurality of successive times, each time to a set of $n$ transducers which is shifted by at least one said transducer of said array of transducers such that scanning occurs throughout said array.

11. A device according to claim 10, wherein the elementary transducers are part-circular strips arranged at equal intervals over a part-cylindrical surface whose radius is equal to the predetermined distance.

12. A device according to claim 10, wherein said phase shift distribution signal is selected for simulating Fresnel zones corresponding to amplitudes applied to the elementary transducers as represented by $A_o \cos \phi_i$ where $A_o$ is a constant and $\phi_i$ is the phase angle.

13. A device according to claim 10, wherein said switch means comprises:

a first set of N electronic switches, each of said first set of electronic switches to selectively apply said signal of frequency $f$ to a different one of said N elementary transducers with a phase angle $\phi$; and a second set of N electronic switches, each of said second set of electronic switches to selectively apply said signal of frequency $f$ to a different one of said N transducers with a phase angle $\phi + \pi$.

14. The device of claim 13, wherein said switch means includes inverter means which applies said signal of frequency $f$ to each electronic switch in said first set of electronic switches with a phase shift $\phi$ and to each electronic switch in said second set of electronic switches with a phase shift $\phi + \pi$.

15. The device of claim 14, wherein said inverter means comprises a transformer having a primary winding connected to said single signal generator and a secondary winding having opposed terminals, one of said opposed terminals being coupled to said first set of electronic switches, the remaining of said opposed terminals connected to said second set of electronic switches.

16. The device of claim 13, wherein each of said electronic switches are transistors.

17. A device for C-mode ultrasonic scanning according to claim 16, further comprising means for moving the transducers as a whole in a direction perpendicular to the scanning direction by predetermined steps after each complete scanning.

18. The device of claim 13, wherein each transducer of said array does not receive said signal of frequency $f$ when both its associated switch in said first set of switches and its associated switch in said second set of switches are open.

19. A device according to claim 13 wherein said means for storing an electrical phase distribution signal comprises:

first and second registers, each said register having $n$ binary locations corresponding to respective ones of said transducers in said group of $n$ adjacent transducers, means for loading the locations of said first register corresponding to those transducers which are to transmit said signal of frequency $f$ at a phase angle $\phi$, in the form of a predetermined binary condition, means for loading the locations of said second register corresponding to those transducers which are to transmit said signal of frequency $f$ at a phase angle $\phi + \pi$, in the form of a predetermined binary condition, said first and second registers being respectively associated with said first and second set of electronic switches for controlling which of said first and second set of electronic switches applies said signal of frequency $f$ to said transducers.

20. A device according to claim 19, wherein said sequencing means comprises:

first and second shift registers each having N binary locations, each location of said first and second shift registers being operatively connected to a different one of said electronic switches of said second and third sets of electronic switches, respectively; and clock means to shift the contents of said first and second registers serially into the first and second shift registers and along said first and second shift registers.

21. A device according to claim 20, wherein said single signal generator comprises a triggered oscillator which delivers a signal pulse of frequency $f$ and of predetermined duration responsive to each clock pulse.

22. A device according to claim 21, wherein said N transducers are in the form of parallel strips on a flat support, further comprising a set of M tranducers associated with receiving means and distributed regularly on said flat support along a direction transverse to the direction of said array of N tranducers.

23. A device for ultrasonic imaging operable in receiving mode, said device comprising:

(1) an array of N identical elementary transducers distributed at equal intervals along a scanning direction and operable at ultrasonic frequency $f$;
(2) a single signal receiver for processing an electronic signal at ultrasonic frequency $f$;
(3) switch means for simultaneously coupling selected ones of $n$ adjacent transducers of said array to said receiver, in sequence, $n$ being an integer greater than 1 and less than N;
(4) means for storing an electrical phase distribution signal representative of the phase at which said signal is to be applied to each of said $n$ adjacent transducers in said array, said electrical phase distribution signal being chosen such that said $n$ adjacent transducers focus ultrasonic energy having a frequency $f$ at a point located at a predetermined distance from said $n$ adjacent transducers;
(5) said switch means also for subjecting the reflected signals received by each of said $n$ adjacent transducers to a phase shift of either $\phi$ or $\phi + \pi$ according to said electrical phase shift distribution signal and summing at least some of said phase shifted reflected signals to form a single signal representative of a characteristic of said object being scanned when said device is operating in said receiving mode; and
(6) sequencing means for causing said switch means to phase shift and combine said reflected signals received by said $n$ adjacent transducers of said array at each of a plurality of successive times, each time to a set of $n$ transducers which are shifted by at least one said transducer of said array of transducers, when said device is operating in said receiving mode, such that scanning occurs throughout the said array in both said transmitting and receiving mode.

* * * * *